US007439376B2

(12) United States Patent
Daly

(10) Patent No.: US 7,439,376 B2
(45) Date of Patent: Oct. 21, 2008

(54) ESTERS WITH ANTIMICROBIAL, BIORESISTANT AND FUNGAL RESISTANT PROPERTIES

(75) Inventor: Thomas Daly, Chicago, IL (US)

(73) Assignee: TPAT IP LLC, Chicago, IL (US)

( * ) Notice: Subject to any disclaimer, the term of this patent is extended or adjusted under 35 U.S.C. 154(b) by 0 days.

(21) Appl. No.: 11/800,569

(22) Filed: May 7, 2007

(65) Prior Publication Data

US 2007/0276038 A1  Nov. 29, 2007

Related U.S. Application Data

(63) Continuation-in-part of application No. 10/603,356, filed on Jun. 25, 2003, now abandoned.

(60) Provisional application No. 60/392,007, filed on Jun. 26, 2002, provisional application No. 60/802,910, filed on May 24, 2006.

(51) Int. Cl.
    *C11D 1/28*  (2006.01)
(52) U.S. Cl. ........................................................ 554/97
(58) Field of Classification Search ........................ None
    See application file for complete search history.

(56) References Cited

U.S. PATENT DOCUMENTS

| 2,421,165 A | 5/1947 | Senkyus ................... 564/367 |
| 2,888,409 A | 5/1959 | Bender et al. ................. 521/76 |
| 3,156,679 A | 11/1964 | Roy, Jr. ................... 526/230.5 |
| 4,109,074 A | 8/1978 | Creighton et al. ........... 526/320 |
| 4,263,424 A | 4/1981 | Buckley et al. ............... 528/85 |
| 4,264,745 A | 4/1981 | Foucht ....................... 521/171 |
| 4,576,625 A | 3/1986 | Norden et al. ............. 504/101 |
| 4,612,152 A | 9/1986 | Kawabata et al. .......... 264/136 |
| 4,851,588 A | 7/1989 | Kupper et al. ............... 568/713 |
| 4,929,474 A | 5/1990 | Avni et al. .................. 427/326 |
| 4,946,372 A | 8/1990 | Avni .......................... 428/325 |
| 5,013,762 A | 5/1991 | Smith et al. ................. 514/713 |
| 5,075,510 A | 12/1991 | Williams et al. ............ 568/713 |
| 5,084,477 A | 1/1992 | Walter et al. ............... 514/461 |
| RE34,929 E | 5/1995 | Kristen ..................... 206/524.8 |
| 5,656,670 A | 8/1997 | Ajoku et al. ................ 514/642 |
| 5,700,586 A | 12/1997 | Lalho et al. ................ 428/507 |
| 5,723,199 A | 3/1998 | Boot .......................... 428/158 |
| 5,798,115 A | 8/1998 | Santerre et al. ............ 424/423 |
| 5,861,074 A | 1/1999 | Wu ............................. 156/229 |
| 5,866,511 A | 2/1999 | Dallmier et al. ............ 504/150 |
| 6,183,825 B1 | 2/2001 | Crook ........................ 428/34.7 |
| 6,294,589 B1 | 9/2001 | Moody ......................... 521/76 |
| 6,533,884 B1 | 3/2003 | Mallik ........................ 156/209 |
| 6,872,459 B1 | 3/2005 | Frisk et al. .................. 428/474 |
| 6,984,278 B2 | 1/2006 | Anderson et al. .......... 156/209 |
| 2002/0143139 A1 | 10/2002 | Chen et al. .................. 528/354 |
| 2003/0166823 A1 | 9/2003 | Daly ............................ 528/44 |

FOREIGN PATENT DOCUMENTS

| DE | 1 943 112 | 3/1971 |
| GB | 2 007 215 A | 5/1979 |
| JP | 2000053502 | 2/2000 |

OTHER PUBLICATIONS

Journal of Chromatography, Apr. 1988, Klemm et al.

*Primary Examiner*—Paul A Zucker
(74) *Attorney, Agent, or Firm*—Clifford Kraft

(57) ABSTRACT

A bromine/nitro moiety linked into the backbone of an ester or other compound over a wide range of occurrence rates provides antimicrobial, bio-resistant and fungal resistant properties for metal working fluids (MWF)s and other coatings. The moiety can be have the bromo and nitro groups linked to the same or different carbon atoms. The present invention also relates to urethanes, urea, amides, imides, carbonates, ethers, siloxanes, and many other types of linkages essential to MWF bases.

4 Claims, 4 Drawing Sheets

ESTERS WITH ANTIMICROBIAL, BIORESISTANT AND FUNGAL RESISTANT PROPERTIES

This is a continuation-in-part of application Ser. No. 10/603,356 filed Jun. 25, 2003, now abandoned, which claims priority of 60/392,007 filed Jun. 26, 2002; this application also claims priority of 60/802,910 filed May 24, 2006. Application Ser. Nos. 10/603,356, 60/392,007 and 60/802,910 are hereby incorporated by reference.

This application also incorporates by reference my other patent application Ser. No. 10/350,928 filed Jan. 23, 2003 entitled Polymers with Antimicrobial, Bioresistant and Fungal Resistant Properties.

BACKGROUND

1. Field of the Invention

The present invention relates to the field of esters and more particularly to esters with bioresistant, fungal resistant and antimicrobial/antifungal properties.

2. Description of the Problem Solved by the Invention

Due to environmental regulation, the use of tin, mercury, lead, and other heavy metals to control the growth of microbes in organic systems is now prohibited. In particular metal working fluids (MWF) and metal working fluid bases suffer a failure mode when attacked by microbes. The problem is especially acute in water extendable and emulsion MWF systems. The attack of the microbes on the MWF base causes the pH of the system to drop, which destabilizes the emulsion and also increases the corrosion of metal parts that are exposed to the attacked fluid. Aside from the obvious problems that microbes cause in MWFs, operator health issues also arise due to continuous exposure to high levels of bacteria.

Current systems in place include the addition of biocides to the fluid to prevent the bacteria from breaking down the MWF. One common biocide in use is the family of isothiazolinones. This product family is generally hazardous to handle and causes sensitization in many people when exposed repeatedly. The sensitization often takes the form of itching all over the body, or hives when any part is in contact with the isothiazolinone. Additionally, the isothiazolinone family is relatively unstable at the alkaline pH that most MWFs are maintained at. This then requires the operator to add more material on a regular basis. Also, the microbes develop a tolerance to isothiazolinones. This again requires the operator to increase the amount of the isothiazolinone in the system.

A second biocide technology is the use of formaldehyde condensates. These materials are generally hazardous, but do not lead to sensitization of the operators in contact with the MWF. The formaldehyde condensates do contribute to free formaldehyde in the workplace, but the results are not consistent as to how much formaldehyde they contribute to the workplace atmosphere. Most formaldehyde condensates are volatile and evaporate. This requires their replenishment on a regular basis even when they are not consumed.

What is needed is a system that uses an ester as the MWF base that is not susceptible to microbial attack. The material fails to act as a food source for the microbes that are able to digest the current MWF bases.

SUMMARY OF THE INVENTION

The present invention relates to an ester that contains an antimicrobial moiety that is linked into the backbone of the molecule. This moiety is, in general, a bromine atom and a nitro (NO2) group linked to one or more of the carbon atoms forming the backbone of the molecule that is the MWF base. While the present invention is directed primarily to esters, the moiety taught should also be effective when linked onto a carbon atom in the backbone of any suitable MWF base molecule. The moiety can appear in the backbone of the MWF base in various levels of occurrence. A preferred occurrence of around 1000 parts per million on a weight basis is effective; however the frequency of occurrence can be as low as 5 parts per million to as high as 99-100%. MWF base types within the scope of the invention include, but are not limited to urethane, urea, amide, ester, carbonate, ether, and siloxane linkages.

It is well known in the art to combine a carboxylic acid and an alcohol in the presence of a suitable catalyst to form an ester. The present invention adds a bromo-nitro substituted alcohol, diol or polyol to a standard alcohol to be used in the ester synthesis. The proportion of substituted compound used is chosen to yield the desired concentration of the moiety in the final MWF base. A preferred diol for the application is bromonitropropanediol or 2-bromo-2-nitro-propane-1-3-diol or simply BNPD. This particular diol is a solid material with varying degrees of solubility in other alcohols and has proven antimicrobial properties.

In addition, BNPD has been shown to have no tetragenecy (cancer causing effects) and is approved by the CFTA at levels of up to 0.1% for use in cosmetics. BNPD has also been used in baby wipes for its antimicrobial properties.

The fact that the active antimicrobial moiety is covalently linked directly into the backbone of the ester reduces its breakdown at the alkaline pHs required of MWFs. In addition, the moiety is not photo-active or decomposed by sunlight or exposure to mineral salts such as calcium chloride, magnesium hydroxide and sodium chloride as are found in hard and softened water.

Because BNPD is a substituted diol, it is a natural reactant to form part of an ester linkage with a carboxylic acid. Also, being a diol, it mixes directly with a wide range of alcohols or polyols and other performance enhancing additives with no difficulty or adverse reactions. In fact, it can be mixed in any desired proportion (to the extent that it is soluble) with any standard alcohol used in synthesizing esters, ethers, or urethane type linkages.

While bromonitropropanediol (BNPD) is the preferred antimicrobial agent because of its proven activity and its benign effects on the environment and on humans, other alcohols, diols or polyols with bromine and nitro groups linked at the same or different carbon atoms can also be incorporated into the backbone of MWF bases. Any other antimicrobial agents that can be linked onto an alcohol reacted linkage are within the scope of the present invention.

Figure 1:
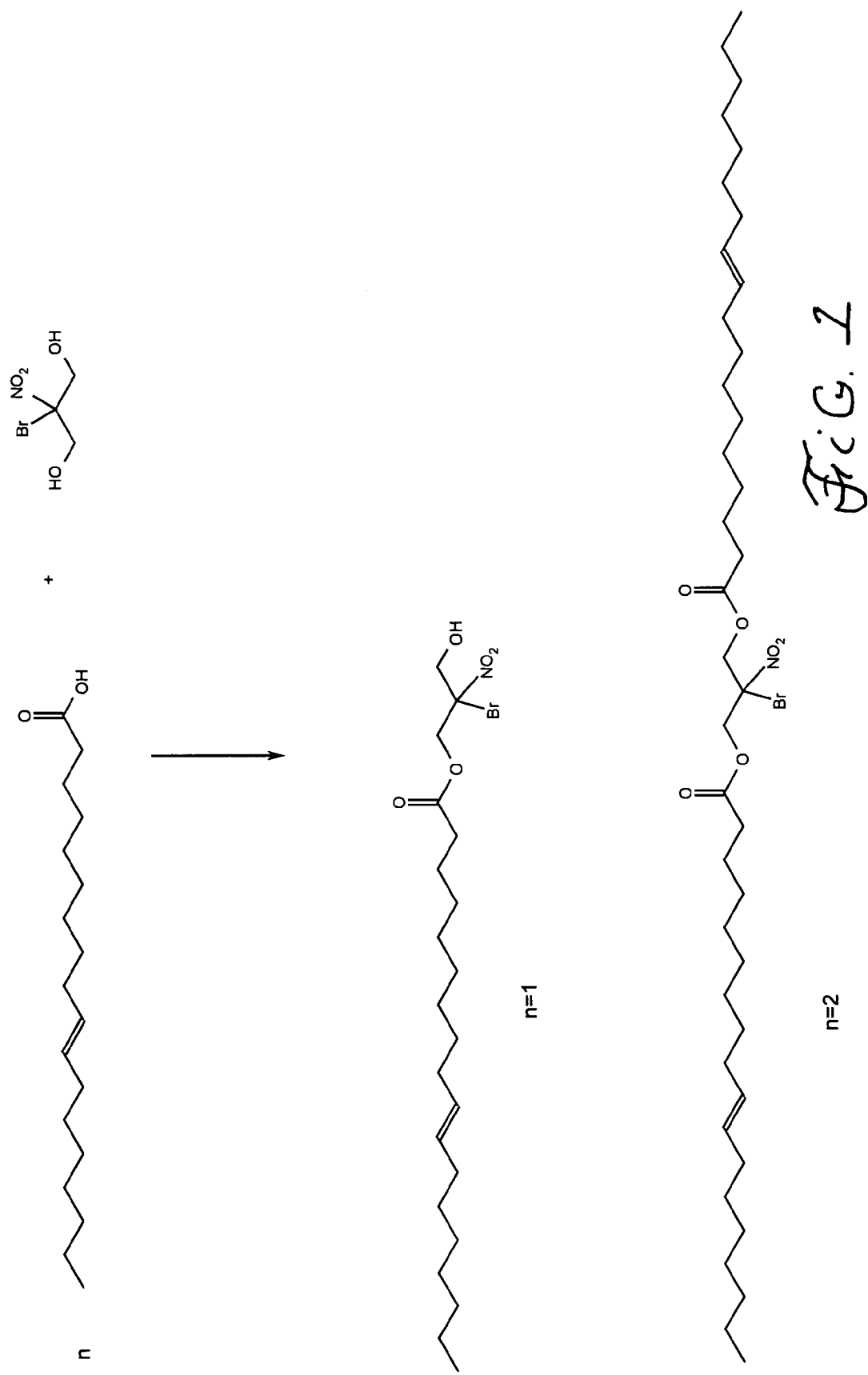
FIG. 1 shows the formation of an ester linkage with BNPD.

Several drawings and illustrations have been presented to aid in understanding the present invention. The scope of the present invention is not limited to what is shown in the figures.

DETAILED DESCRIPTION OF THE INVENTION

It is well known in the art to combine alcohols with carboxylic acids to form ester linkages. One example is isopropyl oleate, the ester of isopropyl alcohol and oleic acid. Polyols are also commonly used, such as in the production of Lexolube 21-214 by Innolex. A typical ester will have the following formula:

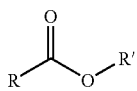

where R typically comes from the original carboxylic acid and R' typically comes from the original alcohol. It is well known in the art that R and R' can be the same or different. The typical example noted above as isopropyl oleate has the following structure:

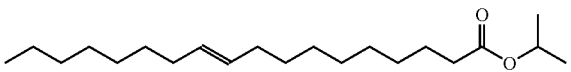

The compound bromonitropropanediol or 2-bromo-2-nitro-propane-1,3-diol (BNPD) has known antimicrobial properties. Tests on this compound have shown that it is effective against various strains of both gram positive and gram negative bacteria in concentrations of 1-50 ppm with the average minimum inhibitory concentration being around 25 ppm. In addition, work has indicated that BNPD is also antifungal. BNPD has the following structure:

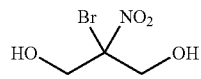

Because BNPD is a polyol, it can be combined with other alcohols, diols, or polyols in the manufacture of the esters used as MWF bases. In particular, BNPD alone or mixed with other alcohols, can be combined with carboxylic acids to form esters that are suitable for use as MWF bases. This causes the active moiety to become covalently linked into the ester. In the case of the oleate ester, the product is:

Or more generally:

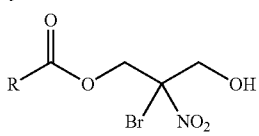

The dioleate ester can easily be made, which has the following structure:

Or more generally, for the diester:

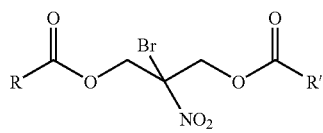

While BNPD is a preferred polyol starting point to link the active moiety into an ester MWF base, it is within the scope of the present invention to use many other materials that contain a bromine atom and nitro group linked near one another. The preferred class of compounds contains the bromine and nitro linked to the same carbon atom; however, it is felt that a moiety where the bromine and nitro are not linked to the same carbon, but near each other will still be effective. Many other similar compounds can also be used. In particular, bromonitromethanediol, bromonitroethanediol, bromonitrobutanediol, etc. can also be substituted into molecule backbones with similar results. It should be understood that these are just examples of the many compounds within the scope of the present invention. The prior art has shown that bromonitromethane is effective for the treatment of nematodes in the soil (See U.S. Pat. No. 5,013,762 which is hereby incorporated by reference) and as a general biocide (See U.S. Pat. No. 5,866,511 which is hereby incorporated by reference). It is felt that bromonitromethanediol and similar diols are equally effective.

The present invention also includes using a BNPD or BNPD analog as the terminus, such as:

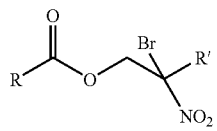

Where R' can be, but is not limited, to CH2OH, OH, CH3, or H.

The present invention reacts BNPD or similar substituted alcohols, diols or polyols, with or without the aid of a solvent or co-solvent, with a carboxylic acid to form the ester MWF base.

The present invention results in a covalently linked bromine/nitro moiety in the backbone of an ester at some frequency of occurrence that provides antibacterial or anti-fungal effects. The present invention relates to ester, urethane, urea, amides, imides, carbonates, ethers, siloxanes, and many other types of linkages essential to MWF bases.

Figure 2:
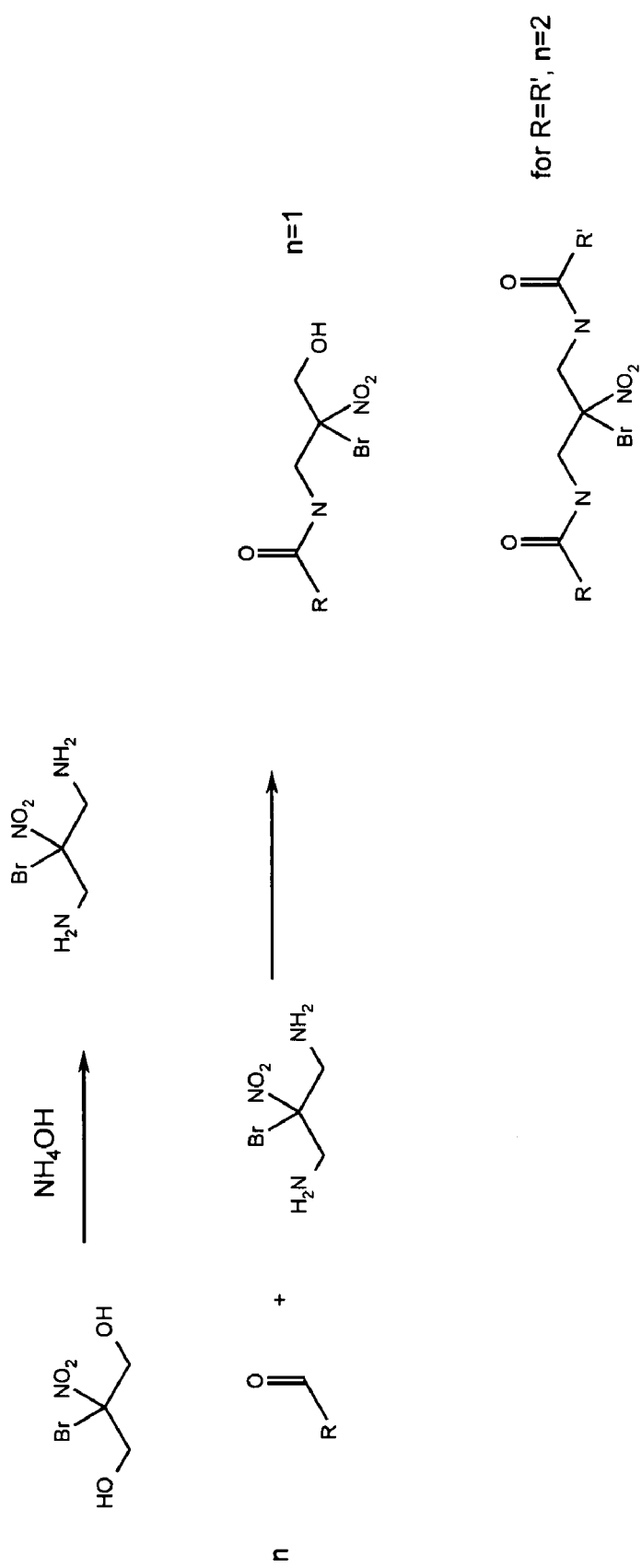
FIG. 2 shows treatment of BNPD with ammonium hydroxide to form an amide.
Figure 3:
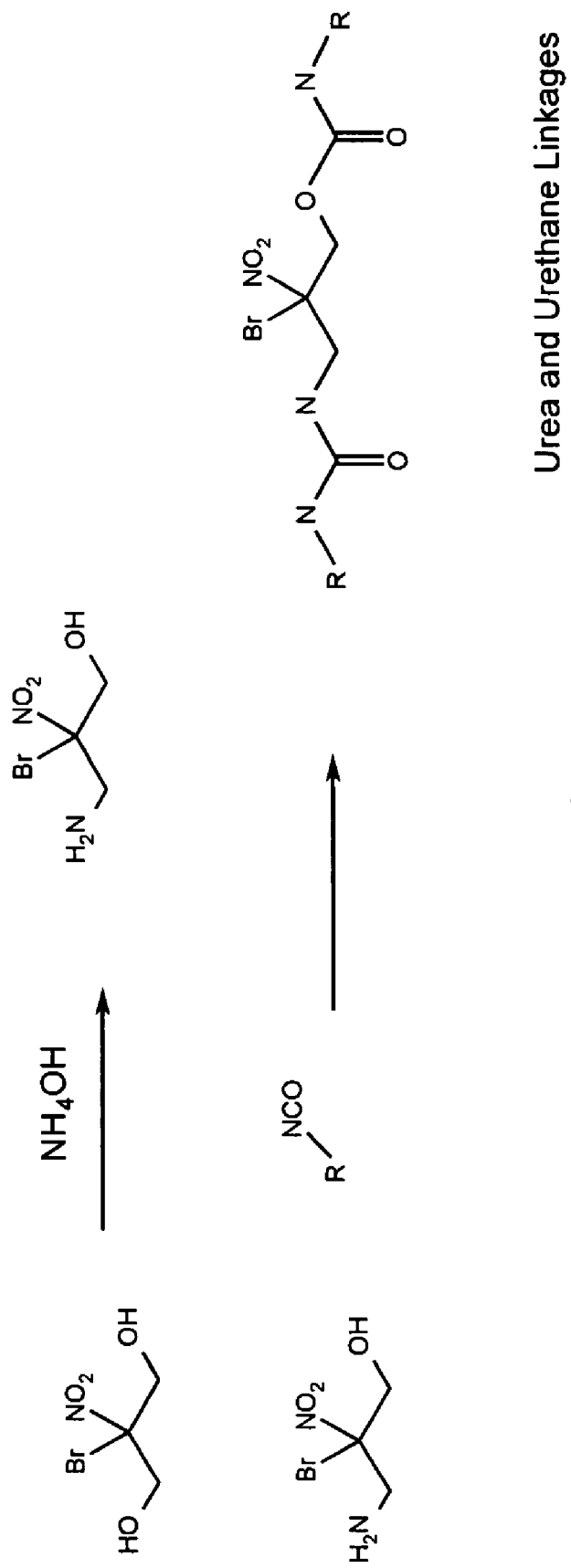
FIG. 3 shows the formation of both urethane and urea linkages.
Figure 4:
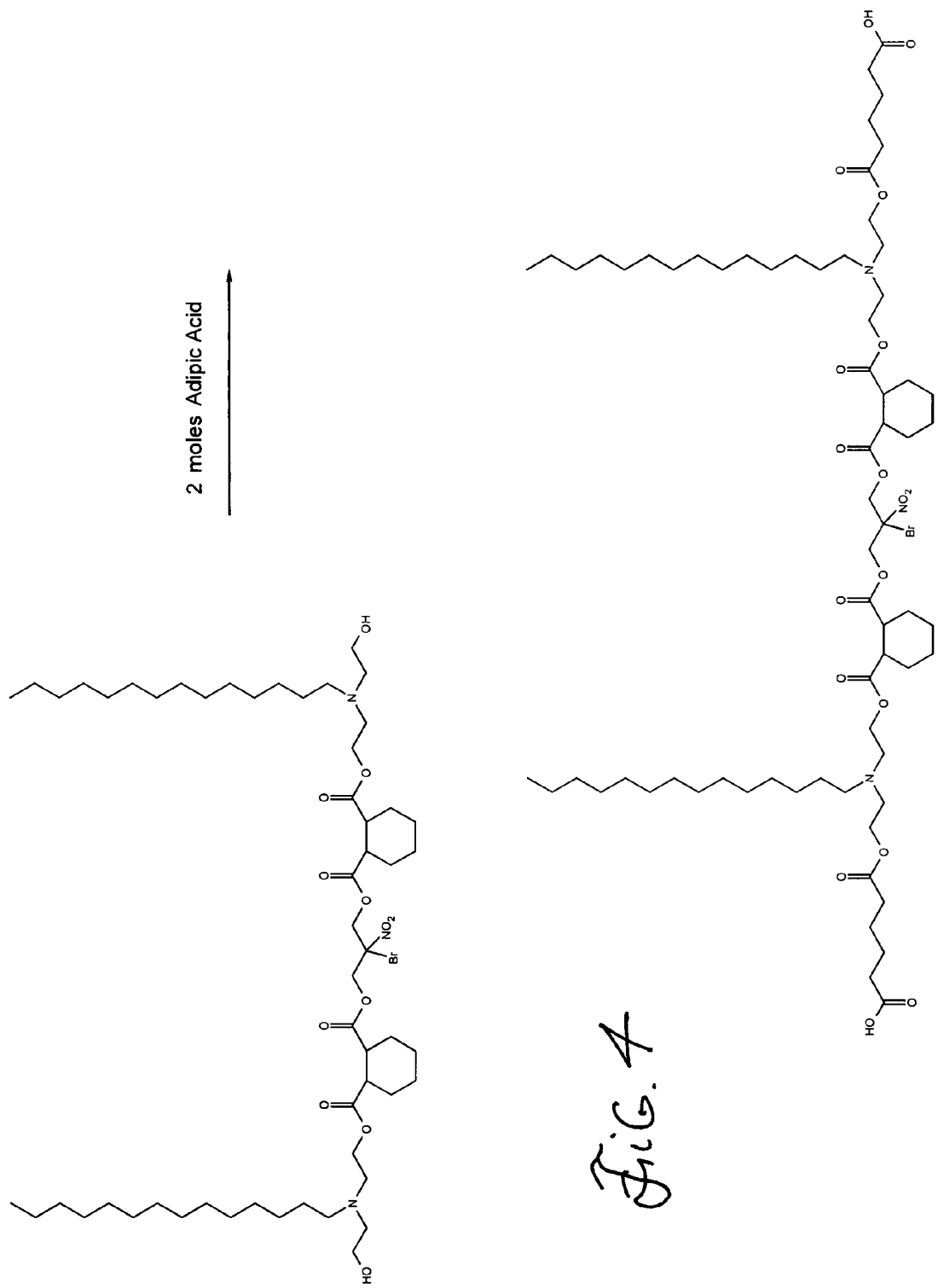
FIG. 4 shows the synthesis of an acid functional, pendant fatty chain.

FIG. 1 shows the formation of an ester linkage with BNPD. FIG. 2 shows treatment of BNPD with ammonium hydroxide to form a bromonitro amine or diamine which can then be combined with an aldehyde or carboxylic acid to form an amide. FIG. 3 shows the formation of both urethane and urea linkages. FIG. 4 shows the synthesis of an acid functional, pendant fatty chain.

The present invention is particularly well suited to use in metal working fluids, not just as an additive, but as a base oil for use in oil soluble cutting oils. The diester structure of the esters of the present invention make them natural components to use as a replacement, in full or in part, of the base oil, particularly in cases where the base oil is a neopentyl glycol ester or diester. The similarity of structure between the esters of the present invention and the neopentyl glycol esters allow the direct substitution of the neopentyl glycol ester while maintaining the desired properties, such as lubricity, with a minimal need for reformulation, while still obtaining the antimicrobial and biostatic properties.

The dialkyl and diallyl forms are not generally water soluble, and may or may not be useful in aqueous systems such as cooling tower water, paper process water, and other industrial process waters; however, the compounds represented by the present invention can be readily emulsified into synthetic, semi-synthetic metal working fluids and water dilutable metal working fluids in general. Replacing portions of the base oil component, such as oil soluble esters or hydrotreated naphthenics (commonly referred to as 100, 200, etc. second oils in reference to their viscosities, or commonly by the tradename HYDROCAL), is one possible way to incorporate the present invention to obtain the benefits of the lubrication and antimicrobial properties.

Embodiments of the present invention wherein R and/or R' include a polyether group, such as, but not limited to, polyethylene oxide, polypropylene oxide and polybutylene oxide, the present invention can act as a surfactant, foaming agent, anti-foam and emulsion breaker depending on the degree of ethoxylation, propoxylation, and/or butoxylation. This embodiment enables the present invention to be used as an emulsifier in water dilutable metal working fluids, and more generally, as a surfactant in any application where a surfactant and an antimicrobial would be beneficial.

The present invention can also function as a corrosion inhibitor. While controlling microbial growth does play an important part in controlling pH, and therefore corrosion, the high electron density of the center of the molecule attracts it to the metal surface and the Alkyl branches that extend out act as a barrier to water and corrosive salts. This typical film forming mode of action of corrosion inhibition can be exploited not only for the time the part being worked is in contact with the fluid, but the draw-out that occurs keeps the present invention on the part surface well after processing. This is a major benefit of the present invention since corrosion is often more of a problem while the part sits between processing steps or prior to packaging and/or shipping.

Further application for the present invention is in so-called spray shower cleaners, such as the FRESH SHOWER® brand by Clorox. Addition of the compounds of the present invention maintains the water sheeting action, while adding a persistent antimicrobial that does not simply wash away. Further, the use of the present invention in this application is safe for many bathroom surfaces such as marble that are damaged by other antimicrobials and even by EDTA (ethylenediamine tetraacetic acid).

Embodiments of the present invention are also useful as a skin surface antimicrobial. They are non-toxic and have very mild handling characteristics. By applying them in a formulation similar to other skin creams and washes, the present invention is expected to be effective against a wide range of skin surface pathogens. Pathogens, such as the fungi that cause yeast infections (*candida*) and athlete's foot (*trichophyton*), as well as more generally those that cause ringworm and many other pathogens can be controlled or eliminated by the present invention. Bacterial skin conditions such as boils caused by various strains of *staphylococcus* bacteria and many other skin bacterial conditions can also be controlled or remedied by the present invention. When properly applied, the present invention can act as a remedy for thrush.

The esters of the present invention make excellent starting materials for sulfonate surfactants. One route, but not the only route, to formation is by reacting the product above with sodium metabisulfite or sodium sulfite. A very useful anionic surfactant can be produced that has strong microbial resistance.

The esters of the present invention can also serve as excellent starting materials for functional replacements of sulfurized fats having strong microbial resistance. One route, but not the only route, is the cross linking or "vulcanizing" of these compounds with sulfur, or other materials, such as transition metal based complexes, including, but not limited to, cobalt and zinc complexes. These produce excellent lubricity aids for metal working fluids and other applications that require higher levels of lubricity and that can benefit from microbial resistance. A specific example of transition metal cross-linkers is cobalt octoate. Conversely, the vulcanizing or cross linking the carboxcylic acids prior to esterification will also produce good results.

The examples and illustrations presented herein are for the purpose of understanding the concepts of the present invention. It will be clear to one with ordinary skill in the art that many other examples and structures are within the scope of the present invention. This applies particularly to classes of linkages where an example of one particular structure has been given; it will be appreciated by one skilled in the art that in such a case, the entire class of compound is within the scope of the present invention.

EXAMPLE 1

Production of a Metal Working Fluid Base

A vessel equipped with vacuum and heat was charged with 109 g (0.531 moles) of undecanoyl chloride and 48 g of BNPD (0.241 moles). The vessel was heated to 60 C. The temperature was held for 3 hours. The BNPD diundecanoate recovered was a translucent light yellow liquid.

I claim:

1. An anionic surfactant of the following structure:

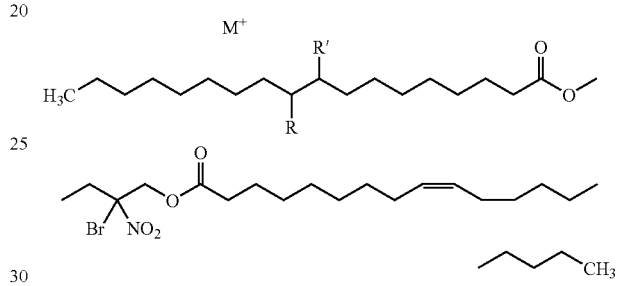

where R is not equal to R' and one of R or R' is —SO$_3^-$ and one of R or R' is H, and where M is a cation or H.

2. The anionic surfactant of claim 1 where M is Na.

3. An anionic surfactant of the following formula:

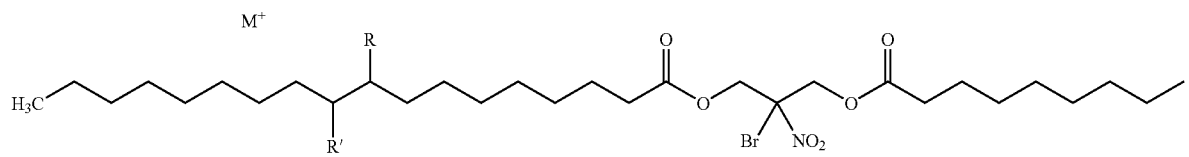

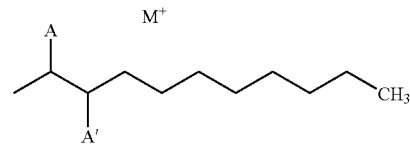

where R is not equal to R' and one of R or R' is —SO$_3^-$ and one of R or R' is H and where A is not equal to A' and one of A or A' is —SO$_3^-$ and one of A or A' is H, and M is a cation or H.

4. The anionic surfactant of claim 3 where M is Na.

* * * * *